United States Patent [19]

Levenson

[11] Patent Number: 5,094,616
[45] Date of Patent: Mar. 10, 1992

[54] DENTAL APPLIANCE

[76] Inventor: Myron Levenson, Timberidge Trail, Gates Mills, Ohio 44040

[21] Appl. No.: 631,632

[22] Filed: Dec. 21, 1990

[51] Int. Cl.$^5$ .............................................. A61C 17/06
[52] U.S. Cl. ........................................ 433/93; 433/91
[58] Field of Search .................... 433/91, 93, 94, 96; 604/902, 266, 268, 35; 128/750

[56] References Cited

U.S. PATENT DOCUMENTS

| | | | |
|---|---|---|---|
| 1,766,341 | 6/1930 | Kulik | 433/91 |
| 2,637,106 | 5/1953 | Otis | 433/91 |
| 2,644,234 | 7/1953 | Scott | 433/94 |
| 3,324,855 | 6/1967 | Heimlich | 433/91 |
| 3,520,300 | 7/1970 | Flower, Jr. | 433/91 |
| 3,758,950 | 9/1973 | Krouzian | 433/91 |
| 4,158,916 | 6/1979 | Adler | 433/91 |
| 4,233,025 | 11/1980 | Larson et al. | 433/91 |

Primary Examiner—Cary E. O'Connor
Attorney, Agent, or Firm—D. Peter Hochberg; Mark Kusner; Louis J. Weisz

[57] ABSTRACT

A dental appliance for use with an aspirator tube which forms part of a dental aspirating system, the system being used for periodically removing saliva/water from a patient's mouth by means of suction. The present improvement is a resilient foam sleeve that fits over the end of the aspirator tube which is inserted into the patient's mouth thereby providing a cushioning effect between the tube and the patient's mouth, a damping effect by reducing the rushing sound that usually accompanies such system, an enhanced suction efficiency between of the increased surface area available for suction and a filtering effect by preventing solid debris from entering the aspirator tube.

3 Claims, 1 Drawing Sheet

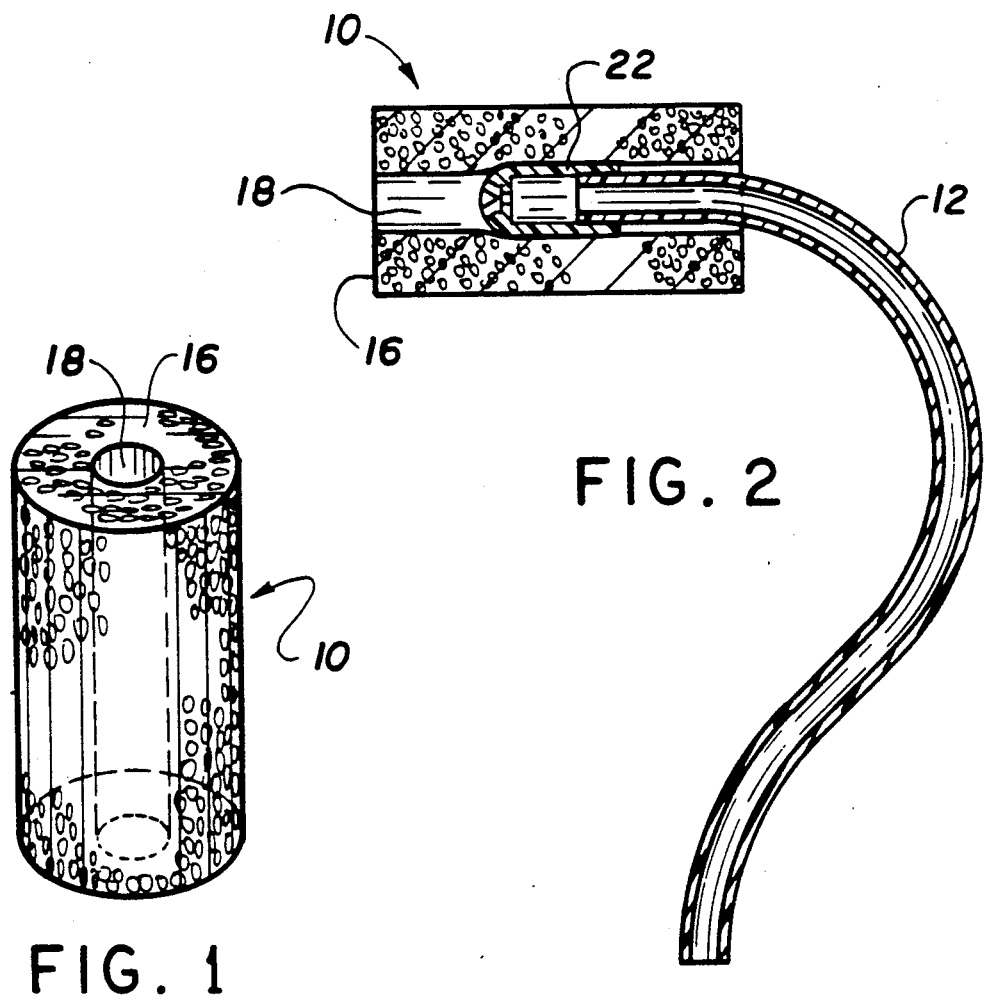
FIG. 1
FIG. 2
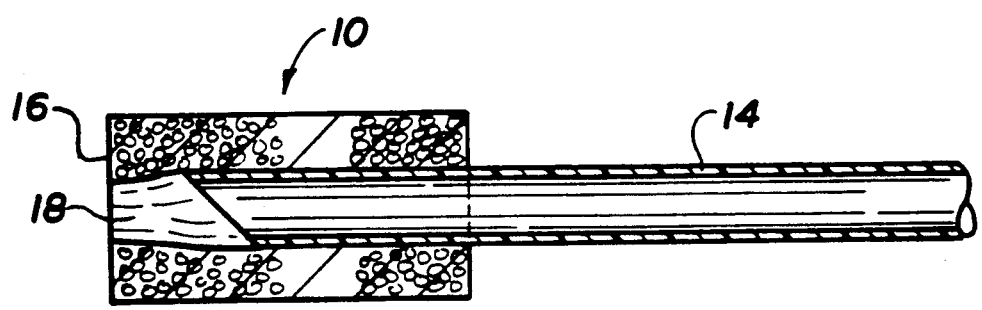
FIG. 3

DENTAL APPLIANCE

FIELD OF INVENTION

The present invention relates generally to dental appliances and more particularly to aspirating systems for evacuating moisture/saliva from a patient's mouth.

BACKGROUND OF THE INVENTION

Aspirating systems for removing water, saliva and foreign matter by means of vacuum, from a patient's mouth are widely used in dental offices and are generally comprised of two types of aspirator tubes. The first type is a high volume aspirator tube which is an elongated, straight tube approximately ½ inch in diameter. This type of aspirator is normally hand-held by a dentist or an assistant within a patient's mouth.

Another type of aspirator tube is a low volume one which is generally hook shaped and dimensioned to rest on the patient's jaw with the free end thereof located within the mouth cavity. This type of aspirator tube has a smaller diameter as compared to the high volume aspirator tubes, that being approximately ¼ inch. Low volume aspirators generally include a perforated cap at the end thereof.

Both types of aspirator tubes are generally formed of metal or hard plastic and produce a very uncomfortable sensation when they come in contact with the soft tissue lining of the mouth cavity of a patient. Areas in the mouth, such as under the tongue, have tissues containing surface glands and blood vessels which are very sensitive and can be easily damaged when such aspirators come in contact therewith.

In this respect, it is not uncommon, especially with a high volume aspirator tube for tissue to be drawn into the orifice of the tube. Also, in a typical aspirating system, once vacuum is applied, a loud rushing noise is produced. This noise together with the tendency for the sensitive tissue to be pulled into the orifice of the tube causes considerable discomfort to the patient.

With respect to low volume aspirators, while the perforated tip and low volume suction, generally reduces the problem of tissue being sucked into the tube, because this type of aspirator is generally hooked onto the patient's jaw, it is not unusual for the tip end, i.e., the free end, of the aspirator to contact and rub against the sensitive tissue lining, thereby irritating the same.

The present invention overcomes these and other problems by a providing a dental appliance which eliminates the discomfort caused by aspirators tubes known heretofore.

SUMMARY OF THE INVENTION

In accordance with one aspect of the present invention, there is provided an appliance for use in combination with a saliva/water aspirator tube in a dental aspirating system wherein one end of said tube is inserted into a patient's mouth to periodically remove collected saliva/water by means of suction. The appliance is comprised of a generally cylindrical resilient sleeve having an inside diameter slightly smaller than the outside diameter of the patient-end of the aspirator tube. The foam sleeve is dimensioned to extend slightly beyond the patient-end of the aspirator tube. The sleeve is formed of a non-toxic, open cell, foam material, has a wall thickness approximately equal to its inside diameter. The pore size and pore density of the improvement foam-sleeve is dimensioned so as to enhance the suction of saliva/water, to prevent solid debris from entering the aspirator tube and to cause the debris to get lodged in the foam sleeve and allow for inspection of trapped material, such as calcareous deposits, fragments of restorative material, root tips, etc. Importantly, the physical characteristics of the foam causes it to form a cushion between the surface of the patient's mouth and the aspirator tube. Also the extending portion of the foam sleeve, reduces by damping, the sound which would normally emanate from such systems.

It is an object of the present invention to provide a dental appliance which eliminates the discomfort associated with aspirator tubes used in dental aspirating systems known heretofore.

Another object of the present invention is to provide an appliance as described above which reduces a likelihood of damage to sensitive tissue lining the mouth.

A further object of the present invention is to provide an appliance as described above which reduces the possibility of soft tissue lining the mouth being drawn into the aspirator.

Another object of the present invention is to provide an appliance as described above which muffles the undesirable suction noises typically associated with dental aspirating systems.

A still further object of the present invention is to provide an appliance as described above which increases the suction efficiency of dental aspirating systems by increasing the surface area available for suction, of dental aspirating systems known heretofore.

A still further object of the present invention is to provide an appliance as described above which filters out solid debris thereby preventing it from entering the aspirating system.

Yet another object of the present invention is to provide an appliance as described above which collects debris found in the mouth and allows evaluation thereof.

These and other objects and advantages will become apparent from the following description of a preferred embodiment of the invention taken together with the accompanying drawings.

BRIEF DESCRIPTION OF THE DRAWINGS

The invention may take physical form in certain parts and arrangement of parts, a preferred embodiment of which will be described in detail in the specification and illustrated in the accompanying drawing wherein:

FIG. 1 is a perspective view of a dental appliance for use with a dental aspirating system illustrating a preferred embodiment of the present invention;

FIG. 2 is a sectional view of the dental appliance shown in FIG. 1 fitted on a typical low volume dental aspirator tube; and FIG. 3 is a sectional view of the dental appliance shown in FIG. 1 attached to a high volume dental aspirator tube.

DETAILED DESCRIPTION OF THE PREFERRED EMBODIMENT

Referring now to the drawings where the showings are for the purpose of illustrating a preferred embodiment of the present invention and not for the purpose of restricting the same, FIG. 1 shows a dental appliance 10 for use with a conventionally known low volume dental aspirator tube 12, shown in section FIG. 2, and a high volume dental aspirator tube 14 shown in section FIG.

3. In the embodiment shown, dental appliance 10 is generally cylindrical and includes an annular wall 16 which defines a cylindrical bore 18 which extends through appliance 10. Bore 18 is dimensioned to have a diameter slightly smaller than the outer diameter of the aspirator tube to be used therewith. In case of the low volume aspirator tube 12, the diameter of the bore is slightly smaller than the outer diameter of the tip of aspirator tube 12 which generally includes a perforated cap 22. The length of the appliance 10 is dimensioned so that a portion of appliance 10 extends beyond the tip of the aspirator tube being used, while simultaneously completely covering the tip of the tube. (See FIGS. 2 and 3). Annular wall 16 is dimensioned to have a thickness approximately equal to the inside diameter of bore 18.

Appliance 10 is generally formed of a non-toxic, open cell, plastic foam material such as polyurethane, rubber, latex, polyethylene or vinyl polymides. According to the present invention, the foam forming appliance 10 is chosen and dimensioned to meet specific operative characteristics. Specifically, the foam must have a pore size (typically measured by pores per linear inch) large enough to permit a reasonable flow of salvia and water therethrough, yet small enough to trap, material and particles, such as calcareous deposits, fragments of restorative material or the like, typically found in a patient's mouth. Further, the foam must be resilient and flexible enough to provide a cushioning effect between the aspirator tube and a patient's mouth, yet not so flexible so as to completely collapse under the weight of the aspirator thereby collapsing the pores of the foam and losing its cushioning affect.

An appliance 10 formed of a polyether based polyurethane material has provided the characteristics desired in the present invention. In this respect, polyurethane foams can be of two types: polyether based and polyester based. The polyether based foam is preferred because of its greater flexibility and because of the higher air flow rate it provides. An operable embodiment of the present invention would include a foam material having a density of 1.5-1.7 lbs./cu. ft., and an indent force deflection (a measure of the compressibility or flexibility of the material) of 41-49 lbs./50 sq. in. The preferred average pore size of such a material would be 35-45 pores per linear inch which yields a preferred minimum air flow of approximately 3 cu. ft./min. All of the above physical properties are measured by test method ASTM D-3574-86.

The above values of the various physical properties define a material suitable for use in the present invention. It is believed that an operable appliance 10 could be formed of a foam material having the following physical characteristics: a density of between 1.3-1.9 lbs./cu. ft.; an indent force deflection of between 35-55 lbs./50 sq. in.; an average pore size of between 30-50 pores per linear inch and a minimum air flow of approximately 2.5 cu. ft./min. It is believed that a density range as listed above would provide a light appliance which would be comfortable to the patient when resting on the delicate lining of the mouth. Summarily, it is believed that the above range of the indent force deflection would provide an appliance which would be sufficiently flexible and resilient, the significance of which will be explained in greater detail below. A pore size range as set forth above would, it is believed, achieve the desired purpose of allowing the fluid material to pass through and filter out the solid debris. In this respect the pore size affects the minimum air flow rate, which is a measure of the suction efficiency, and it is felt that the minimum air flow rate given above would achieve the desired objective of providing adequate suction efficiency.

Referring now to the operation of the present invention, it will be understood that unless otherwise specified, the description applies equally to the low volume aspirator tube 12 and the high volume aspirator tube 14.

Depending on whether low volume or high volume suction is desired, appliance 10 is inserted over the free end of low volume aspirator tube 12 or the free end of high volume aspirator tube 14, respectively, until it reaches a particular position relative to the respective tubes as shown in FIGS. 2 and 3. The other end of the aspirator tube is connected to the aspirating system which would typically include a vacuum creating device such as a vacuum pump (not shown). With respect to a low volume, the aspirator tube with appliance 10 thereon is inserted into the mouth of the patient so that the weight of tube rests on appliance 10 and not the surface of the patient's mouth. Because of its flexibility, the appliance provides a cushioning effect between the tip of the aspirator tube and the surface of the patient's mouth. This reduces the discomfort associated with the tip resting directly against the patient's mouth and also prevents the sensitive tissue in that area from being drawn into the aspirator tube and causing hematomas, blood swelling, lacerations or punctures. Importantly, vacuum is then applied to the aspirating system which causes the saliva/water to be drawn into the aspirating tube via the pores. As indicated above, the pore size of appliance 10 is important and is preferably dimensioned to be small enough to prevent solid debris from entering the system, yet large enough to permit saliva/water to pass through. The pore size affects the pore density, both of which affect the suction efficiency by providing a larger surface area for suction as compared to an aspirator tube without the appliance. Importantly, this larger surface area acts to reduce contaminated splatter and air borne spray or mist by providing a larger suction surface. Additionally, solid debris does not pass through the pore of appliance 10, but rather gets lodged in appliance 10 so as to allow for inspection by the dentist. The portion of appliance 10 which extends beyond the tip of the aspirator tube, besides providing a cushioning effect also muffles the rushing sound which normally accompanies an aspirating system once vacuum is applied.

The present invention has been described with respect to a preferred embodiment. Modifications and alterations will occur to others upon the reading and understanding of the specification. It is intended that all such modifications and alterations be included insofar as they come within the scope of the invention as claimed or equivalents thereof.

What is claimed is:

1. In combination with a saliva/water aspirator tube typically used in dental aspirating systems wherein one end of said tube is inserted into a patient's mouth to periodically remove collected saliva/water by means of suction, the improvement which comprises:

a generally cylindrical resilient foam sleeve open at both ends thereof having an inside diameter slightly smaller than the outside diameter of the patient end of said aspirator tube, so as to fit snugly over the patient end of said aspirator tube, said foam sleeve extending slightly beyond the patient end of said aspirator tube in order to form a cushion between the surface of said patient's mouth and said aspirator tube and to reduce by damping the sound which would normally emanate from such systems, said foam sleeve being formed from a non-toxic, open cell, plastic material having a wall thickness approximately equal to its inside diameter, a density of 1.5–1.7 lbs./cu. ft., an indent force deflection of 41–49 lbs./50 sq. in., and an average cell size of 35–45 cells per linear inch so as to provide a minimum air flow of 3 cu. ft. per minute thereby enhancing the suction of saliva/water while simultaneously preventing solid debris from entering said aspirator tube and causing it to be lodged in said foam sleeve in said cells, facilitating visual inspection thereof.

2. A dental appliance for use with a saliva/water aspirator tube typically used in dental aspirating systems wherein one end of said tube is inserted into a patient's mouth to periodically remove collected saliva/water by means of suction, said appliance comprising a resilient hollow cylinder open at both ends thereof, formed from a non-toxic, open cell, plastic foam material, said cylinder having an inside diameter slightly smaller than the outside diameter of the patient-end of said aspirator tube, so as to fit snugly over the patient-end of said aspirator tube, said cylinder extending slightly beyond the end of said aspirator tube so as to form a cushion between the surface of said patient's mouth and the end of said aspirator tube and to reduce by damping the sound which would normally emanate from such systems, said cylinder having a wall thickness approximately equal to its inside diameter, a density of 1.5–1.7 lbs./cu. ft., an indent force deflection of 41–49 lbs./50 sq. in., and an average cell size of 35–45 cells per linear inch, so as to provide a minimum air flow of 3 cu. ft. per minute thereby enhancing the suction of saliva/water while simultaneously preventing solid debris from entering said aspirator tube and causing it to be lodged in said cylinder in said cells, facilitating visual inspection thereof.

3. A method for evacuating liquid from the mouth of a patient by means of an aspirator tube during dental operations while simultaneously causing minimal patient discomfort, preventing solid debris from entering said tube, minimizing sound caused by said dental operations and increasing suction efficiency, said method comprising the steps of:

(a) inserting one end of an aspirator tube which is open at both ends into the mouth of a patient, said end of said aspirator tube including a flexible hollow cylinder formed from a non-toxic, open cell, foam plastic material having a density of 1.5–17 lbs./cu. ft., an indent force deflection of 41–49 lbs./50 sq. in., and an average cell size of 35–45 cells per linear inch so as to provide a minumum air flow of 3 cu. ft. per minute thereby enhancing the suction of saliva and water;

(b) positioning said cylinder on said tube so as to extend a pre-determined distance beyond said end of said aspirator tube;

(c) positioning said aspirator tube with said cylinder on it inside the mouth of the patient so that the weight of tube rests on said cylinder and not on the surface of the patient's mouth thereby causing the extending portion to form a cushion between the surface of said patient's mouth, and the end of said aspirator tube, and to dampen the sound that would otherwise emanate from such operations; and (d) applying an appropriate vacuum to the other end of said tube, thereby causing saliva and water to be suctioned into the tube but preventing solid debris from entering said tube, by trapping it in said cells thereby increasing suction efficiency and making said debris available for visual inspection.

* * * * *